(12) United States Patent
Peltier

(10) Patent No.: US 8,744,827 B2
(45) Date of Patent: Jun. 3, 2014

(54) METHOD FOR PREPARING A PROCESSED VIRTUAL ANALYSIS PLATE

(75) Inventor: Eric Peltier, Clamart (FR)

(73) Assignee: Novacyt, Velizy Villacoublay (FR)

( * ) Notice: Subject to any disclaimer, the term of this patent is extended or adjusted under 35 U.S.C. 154(b) by 0 days.

(21) Appl. No.: 13/201,102

(22) PCT Filed: Jan. 25, 2010

(86) PCT No.: PCT/FR2010/050102
§ 371 (c)(1), (2), (4) Date: Aug. 11, 2011

(87) PCT Pub. No.: WO2010/092271
PCT Pub. Date: Aug. 19, 2010

(65) Prior Publication Data
US 2011/0313746 A1    Dec. 22, 2011

(30) Foreign Application Priority Data
Feb. 13, 2009 (FR) ...................... 09 50950

(51) Int. Cl.
*G06G 7/58* (2006.01)
*G06G 7/60* (2006.01)

(52) U.S. Cl.
USPC ............... 703/11; 382/132; 382/133; 702/19

(58) Field of Classification Search
CPC .......... G06T 2207/20108; G06T 2207/20104; G06T 2207/30004
USPC ......................................... 703/11
See application file for complete search history.

(56) References Cited

U.S. PATENT DOCUMENTS

| 6,026,174 A | 2/2000 | Palcic et al. |
| 7,330,309 B2 * | 2/2008 | Tafas et al. ............ 359/396 |

(Continued)

FOREIGN PATENT DOCUMENTS

| EP | 1324097 | * | 7/2003 |
| EP | 1546709 | * | 9/2007 |
| WO | WO 01/84209 | * | 11/2001 |

OTHER PUBLICATIONS

Diallo et al. Computerized Medical Imaging and Graphics 22 (1998) 275-289.*

(Continued)

*Primary Examiner* — Michael Borin
(74) *Attorney, Agent, or Firm* — Young & Thompson

(57) ABSTRACT

The invention relates to a method that includes the following steps:
carrying out a treatment of a sample, the treatment being carried out for differentiating diseased cells from healthy cells in the sample (4);
carrying out at least one first image acquisition of the sample (4) provided on an analysis plate (8) so as to obtain a plurality of images, each representing an area (18) of the analysis plate, said images being arranged side by side so as to form an image of the entirety of the sample in order to create a virtual analysis plate (2),
locating a reference plane of the analysis plate including a slide and a lamella provided above the slide for image acquisition, said reference plane being defined by the surface of the slide or the lamella; and
carrying out at least one second image acquisition, said second acquisition being carried out at a different thickness of the sample relative to the first acquisition so as to obtain a plurality of images corresponding to a section of the sample with a different thickness.

18 Claims, 3 Drawing Sheets

(56) References Cited

U.S. PATENT DOCUMENTS

| | | | |
|---|---|---|---|
| 7,596,249 B2* | 9/2009 | Bacus et al. | 382/128 |
| 2002/0114497 A1 | 8/2002 | Wetzel et al. | |
| 2003/0004905 A1* | 1/2003 | Reading et al. | 706/15 |
| 2004/0004614 A1 | 1/2004 | Bacus et al. | |
| 2004/0227937 A1* | 11/2004 | Richardson | 356/244 |
| 2005/0123181 A1* | 6/2005 | Freund et al. | 382/128 |
| 2006/0215888 A1* | 9/2006 | Habets et al. | 382/128 |
| 2007/0103693 A1* | 5/2007 | Everett et al. | 356/479 |
| 2008/0032328 A1 | 2/2008 | Cline et al. | |

OTHER PUBLICATIONS

Schmitt et al. (Micron vol. 28. No. 3, pp. 197-215, 1997.*

French Search Report, dated Sep. 9, 2009, from corresponding French application.

International Search Report, dated Jun. 25, 2010, from corresponding PCT application.

* cited by examiner

METHOD FOR PREPARING A PROCESSED VIRTUAL ANALYSIS PLATE

FIELD OF THE INVENTION

The present invention relates to a method for preparing a virtual analysis plate of a cytological sample positioned on an analysis plate in order to allow a cell analysis of said sample, of the type comprising the following steps:
  carrying out a treatment of the sample, said treatment being carried out for differentiating pathological cells from healthy cells in the sample,
  carrying out an acquisition of images of the sample positioned on the analysis plate so as to obtain a plurality of images, each image representing an area of the analysis plate, said images being arranged side by side so as to form an image of the entirety of the sample in order to create a virtual analysis plate.

The invention particularly applies to cytological analysis methods.

The analysis of samples is for example used for the diagnosis of pathologies, from cells sampled by smearing (cervical, vaginal or other smears), by the puncture of organs (breasts, thyroid, ganglion or other organs) or further by collection (urine, broncho-alveolar lavage or other fluids), in order to detect any type of pathology and more particularly precancer or cancer conditions.

BACKGROUND OF THE INVENTION

In a known way, the samples are examined by specialized and trained observers for detecting cells which may be pathological in a sample positioned on an analysis plate or slide. In order to allow the detection of potentially pathological cells, the sample undergoes a treatment, such as staining with which it is possible to show i.e. the characteristics of the nucleus and the cytoplasm of the cells in order to assist with locating and diagnosing pathological cells. When the sample is observed, the potentially pathological cells then show differences in tinctorial affinities, in size and shape, both at the nucleus and at the cytoplasm with respect to normal cells.

The analysis may be accomplished manually, without any particular assistance. In this case, the physician or specialized technician scrolls through the sample plates under a microscope and observes each of them with view to detecting morphological abnormalities indicating pathological cells which may correspond to a precancer or cancer condition for example. Such an analysis method is tedious and is considerably time-consuming. Further, it does not provide any satisfactory results especially with a number of "false negatives" estimated to be about 30%, i.e. of samples considered as normal while there exists a pathology in the patient, notably a precancer or cancer pathology with the risks of subsequent development of cancer in a wrongly reassured patient.

In order to improve the results of the analysis, it was proposed to improve the sampling, i.e. the number of cells, their fixation, their staining and their spreading out on the analysis plate, but also to assist the physician or specialized technician in his/her analysis, for example by computer analysis means, such as image processing software and other means.

For this purpose, a camera or a still camera is used for acquiring images of the different areas of the sample positioned on the analysis plate and transmitting the data of these images to a computer system which then operates on a <<virtual>> analysis plate.

This computer system allows processing of the signal, pre-processing of the images and a comparative analysis of the images with optionally newly generated or existing databases in order to accelerate the analysis process, and thereby allow a larger number of samples to be analysed and to assist the physician or specialized technician. The images of a sample are for example examined automatically and, if certain areas having an abnormality are recorded, the corresponding images are passed on to a physician or specialized technician who may then determine whether these areas show pathological cells or not. The physician or specialized technician therefore observes nothing more than abnormal areas without analyzing the areas considered as normal by the computer system. Such a method actually allows an acceleration of the analysis and makes the diagnosis more reliable.

However, the physician or specialized technician then no longer has the opportunity of observing normal samples or samples having minor morphological changes, which is detrimental to his/her appreciation of the samples and especially to his/her learning curve or even to the preservation of his/her diagnostic acuity. Indeed, the analysis of samples is based on the training and practice of the physician or specialized technician in examining samples and in comparing normal areas and areas having abnormalities. The fact of suppressing this practice by a computer-aided analysis may lead physicians or specialized technicians to lose their skills and thereby causing errors in analysis.

Further, contrary to the field-by-field scanning the line-by-line scanning of a color image requires the deletion or Red/Green/Blue (RGB) registration which needs a high level of adjustment for the alignment of the images, this high adjustment level being sensitive to the slightest vibrations. Consequently, this line-by-line scanning for a color image may take a long time because of the processing operations applied on the slide during the scanning. Further, the scanning of a color image requires significant image compression times.

Moreover, the scanning is delicate for samples containing three-dimensional clusters of cells, i.e. <<stacks of cells>>, notably of pathological cells. Indeed, the focusing by the camera is accomplished at a thickness of the cluster defined by one or more focal points at the cluster, leaving the other deeper or more superficial points in the fuzziness. In order to obtain a proper <<large field>> image, i.e. of the entirety of the analysis plate, for a screening or diagnostic read-out on the single virtual plate, it is required to have a "blurred" surface as small as possible (less than 5%). Further, the segmentation tools are more difficult to handle on blurred areas affecting both the isolated cells and the three-dimensional clusters. Consequently, the analysis of the cells and the nuclei becomes much less relevant and may even cause poor categorization of the cells.

The invention aims at overcoming the drawbacks mentioned above by proposing an analysis method which, while allowing time to be saved in the scanning processes, makes it more performing in terms of surface that can be analysed, and more performing in terms of quality of detection of cell abnormalities for computer aided analysis, within the scope of a more relevant quality control associating diagnostic check points and diagnosis training points for the physician or specialized technician.

SUMMARY OF THE INVENTION

For this purpose, the invention relates to a method of the aforementioned type, characterized in that it comprises the following steps:
  locating a reference plane of the analysis plate comprising a slide or a lamella positioned above the slide, for acquiring images, said reference plane being defined by the surface of the slide or of the lamella; and carrying out at least a second image acquisition, said second acquisition being carried out at a thickness of the sample different from that of the first acquisition, so as to obtain a plurality of images, corresponding to a section of the sample made at a different thickness.

With such a method it is possible to produce in a particularly simple way at least one image of a sample allowing the detection of possible pathological cells and the acquisition of a large amount of information on the sample, as this will be described later on.

According to other characteristics of the preparation method:

the location of the reference plane of the analysis plate is accomplished by acquiring a topographic image of the slide or of the lamella, the analysis plate comprises at least one test pattern laid out so as to locate the reference plane for the image acquisition regardless of the thickness of the sample positioned on the analysis plate, said image acquisition being carried out at a defined thickness relatively to the reference plane of the slide or lamella defined by the test pattern, the analysis plate comprises at least four test patterns positioned around the sample, said or each test pattern is printed on the analysis plate, the thickness of the sample for the image acquisition is adjustable, the method further comprises a step of superposing data of the acquired images during the acquisition of the images and data of the acquired images modified during the processing of the acquired images, so as to produce only a single large field virtual image shot, the acquisition of images of the sample positioned on the analysis plate is carried out according to a grey level scale, the method further comprises the following step:

carrying out on the virtual analysis plate, processing of the acquired images so as to obtain a virtual restitution of the colors and the intensity of the colors of the cytoplasm and/or the nucleus of the cells of the sample, said colors and said intensity being able to be modified according to the preferences of the person in charge of the analysis, the treatment on the sample is a nuclear staining step or cytological staining, said treatment being laid out so as to make the cytoplasm almost transparent and to enhance the contrast between the nucleus and/or the cytoplasm RNA of the cells and the cytoplasm, the processing of the acquired images corresponds to polychrome virtual recoloration of the Papanicolaou, Schorr, May Grunwald Giemsa or Giemsa type or monochrome type of these acquired images, the virtual recoloration level of the acquired images is adjustable, the method comprises a step for displaying the virtual analysis plate, the method comprises the following steps:

automatically scrolling the large field images acquired from the sample, without displaying additional data; and automatically stopping the scrolling if at least one abnormality which may signify the presence of a pathological cell, is detected by the automatic analysis system, the automatic stopping of the scrolling if at least one abnormality which may signify the presence of a pathological cell, is detected, comprises a step for displaying the enlarged analysis plate at the abnormality and for secondarily displaying information on the displayed sampled area and/or on the entirety of the sample and/or on the patient on which the sample was taken and/or on the result of additional examinations carried out on the sample, the method comprises a step of enlarging the virtual analysis plate in order to allow viewing of a detail of said plate.

BRIEF DESCRIPTION OF THE DRAWINGS

Other aspects and advantages of the invention will become apparent upon reading the following description, given as an example and made with reference to the drawings, wherein.

DETAILED DESCRIPTION OF THE INVENTION

Figure 1:
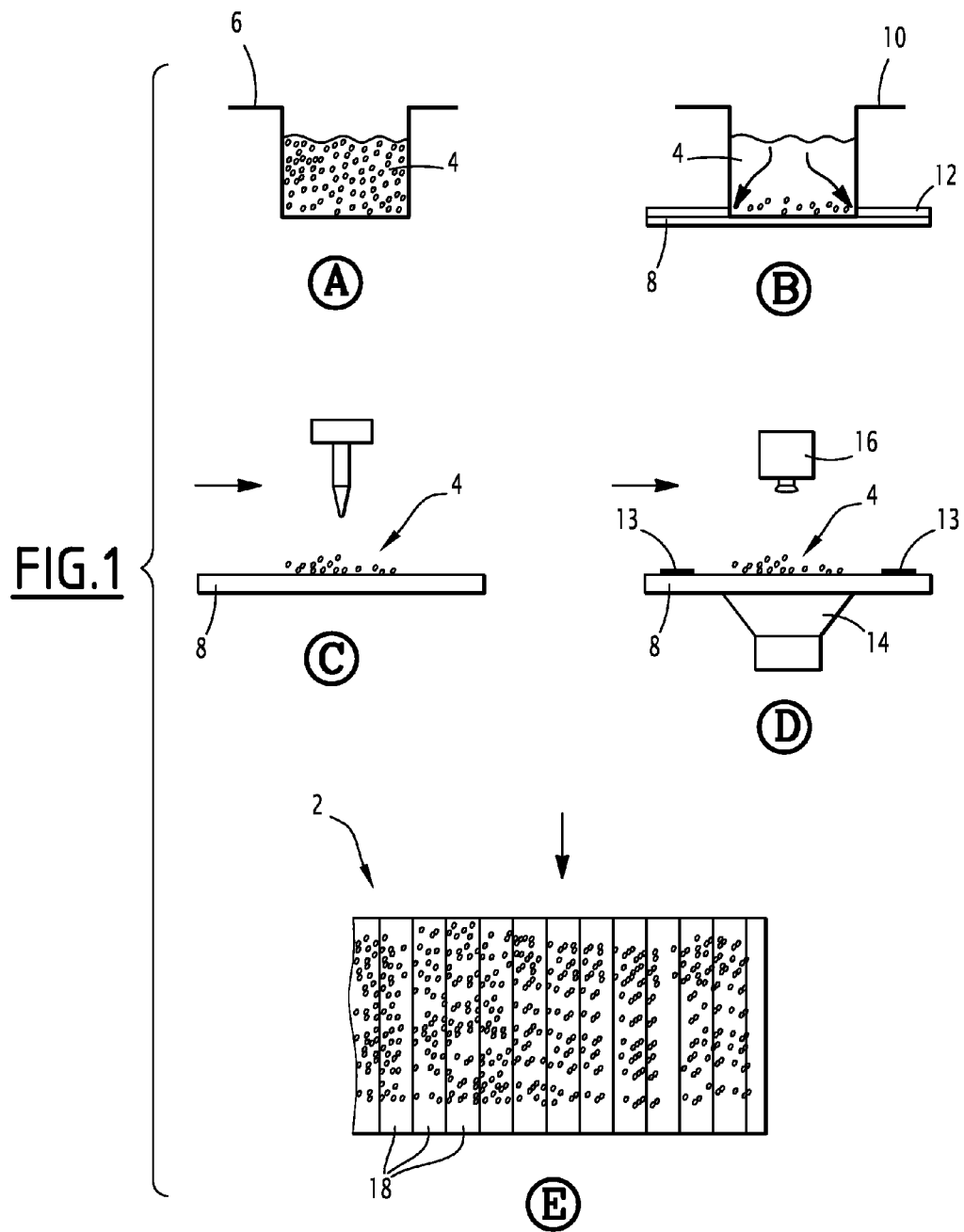
FIG. 1 is a schematic illustration of the different steps of the method for the preparation of a virtual analysis plate according to the invention.

With reference to FIG. 1, a method for preparing a virtual analysis plate 2 is described with view to its cell analysis assisted by a computer system. By virtual plate 2 is meant a set of grouped information and digital data concerning a sample 4.

The sample 4 is for example obtained by smearing (cervical, vaginal smears or others), by puncture of organs (breasts, thyroid, ganglion or other organs) or further by collection (urine, broncho-alveolar lavage or other fluids). During a first step A, the sample is suspended for example in a sample tube or flask 6.

During a step B, the sample 4 is positioned on an analysis plate 8. In a known way, the deposition of the cells onto the plate 8 is accomplished for example by decantation. The sample is poured into a decantation chamber 10, the bottom of which is open on the analysis plate 8. Absorption means 12 allows the absorption of the solution gradually as the cells are deposited on the analysis plate 8. Such a deposition method is known and will not be described in detail her.

During a step C, the sample undergoes a treatment aiming at marking/staining the nuclei, the DNA and/or RNA of the cells by very clearly enhancing the contrast with respect to the cytoplasms of the same cells. Such a marking allows the nuclei to be properly segmented so as to study them morphologically and for quantitating the DNA (for analysis of ploidy for example) and/or the RNA in order to locate potentially pathological cells.

This marking is for example accomplished automatically by means of a robot provided with pipeting means used both for putting the sample 4 into solution and for depositing the cell suspension on an analysis plate 8.

The step B for decantation of the cell suspension may be accomplished before or after the step C for marking/staining as described above.

This marking is preferably accomplished with hematoxylin.

A marker which is different from the markers used for DNA quantification may be used, such as hypericin or a specific marker of proliferation or pathogenic agents, such as for example oncogenic viruses of the Human Papilloma Virus type, in the case of a cervical smear.

Other colorations used in the state of the art may be used, but they have drawbacks. Thus, stoichiometric staining may be contemplated, which provides staining of the nuclei in proportion to the amount of DNA, which allows its quantification, and therefore the marking and analysis of pathological cells within the scope of ploidy.

However, this particular staining, when this is a Feulgen staining for example, is <<technically>> incompatible with Papanicolaou staining and therefore requires redoing cell spreading on the slide for analysis by the physician or specialized technician. Certain industrialists have tried to associate stoichiometric coloration with Papanicolaou staining and have therefore used a stain containing thionine and requiring fixation with methanol which is toxic, and especially which modifies the Papanicolaou staining in its interpretation, notably with nuclei for which the chromatin appears to <<black>>, for fine analysis of the composition of said nuclei, and therefore entails a difficulty in analysis for diagnosing precancer or cancer conditions.

During step D, the analysis plate 8 which comprises the sample 4 stained by a known nuclear stain or a known cytological stain but modified so as to make the cytoplasm almost transparent, is subject to illumination with white light 14 in order to acquire images of the sample 4 by means of the image acquisition device 16.

Image acquisition in white light gives the possibility of obtaining images of the sample colored by the nuclear stain or the modified cytological stain, keeping cytoplasms almost transparent in order to increase the contrast with the nuclei.

With the image acquisition apparatus 16, it is possible to obtain black and white images, more specifically on a grey level scale. With such a selection, it is possible to have a faster image acquisition and with a better resolution than if the acquisition was carried out in color.

The acquisition of images in white light requires that a reference plane is located beforehand. This reference plane of the analysis plate defines a reference thickness relatively to which the thickness of the sample is measured, and as a topographical survey of the surface and of its unevenness.

Figure 2:
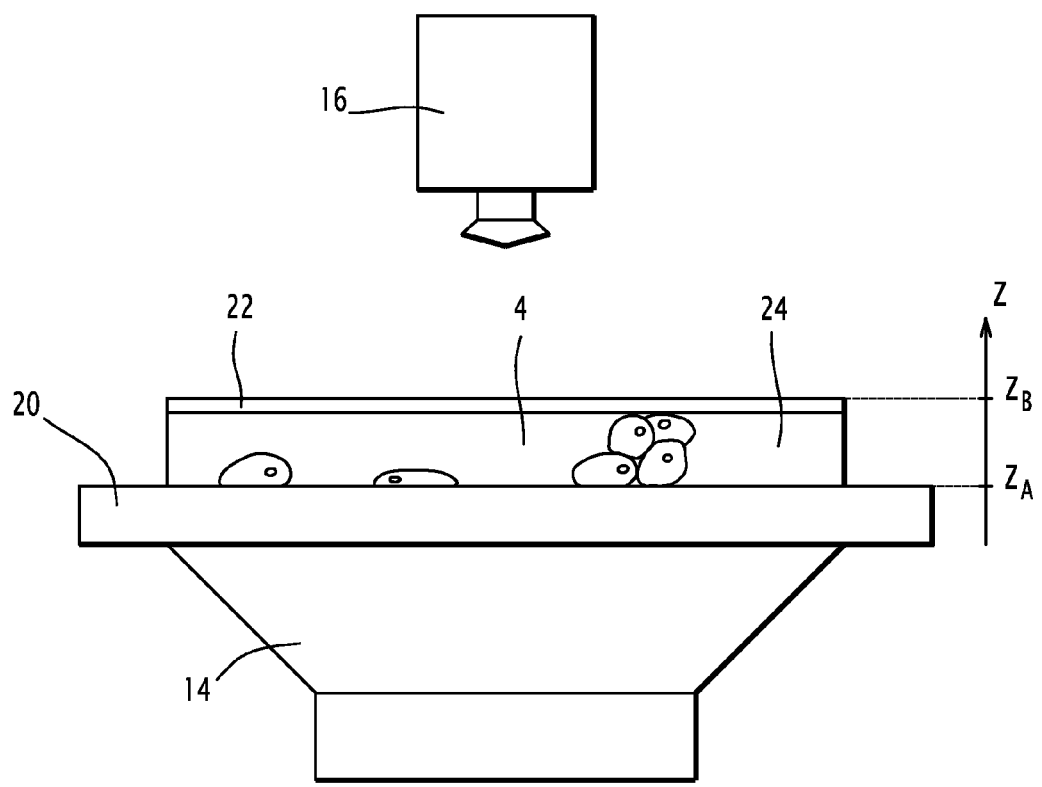
FIG. 2 is a schematic sectional illustration of a sample analysis plate and a device for scanning the slide.

With reference to FIG. 2, the analysis plate 8 comprises a slide 20 and a lamella 22 positioned above the slide 20. The sample 4 of the specimen being positioned between the slide 20 and the lamella 22, and held by the adhesive 24.

The reference plane of the analysis plate 8 is defined either at the upper face of the slide 20, designated by the thickness $Z_A$, or at the upper face of the lamella 22 designated by the thickness $Z_B$.

According to an embodiment, the localization of the reference plane is obtained by acquiring an image of the slide or of the lamella, for example by reflection of ultrasonic waves or light on the slide or lamella with or without any specific treatment of the slide.

This treatment for example consists of making the slide or lamella at least partly reflective.

Before acquiring images in white light, the localization step of the reference plane of the analysis plate makes it possible to avoid a focusing step on the cells and the problems of polymerization of the adhesives for glass lamella or possible bubbles present in the sample. The acquisition of images in white light gives the possibility of obtaining, at different thicknesses located with respect to the reference plane, several planes for a focusing step, secondarily processed, in order to make it optimum. It also gives the possibility of getting rid of the problems of horizontal adjustment of the apparatus. Indeed, the definition of the reference plane allows the <<registration>> of the image with respect to this plane.

Thus, the adjustment of the apparatus relatively to the plate does not require such a high precision as in the prior art.

According to another embodiment, the analysis plate 8 comprises at least one test pattern 13 arranged in order to locate the reference plane of the analysis plate before acquiring images of the sample.

According to an alternative, the analysis plate 8 comprises at least four test patterns 13 arranged so as to be uniformly distributed around the sample, for example the four cardinal points. According to an embodiment, said or each test pattern 13 is printed on the analysis plate 8. According to another embodiment, said or each test pattern 13 is attached on the analysis plate 8, on the slide or on the lamella.

Further, in order to properly view three-dimensional cell clusters during scanning, the image acquisition is carried out at one or several different thicknesses of the sample.

These different thicknesses at which the image acquisition is carried out may be selected prior to the acquisition and are located with respect to the reference plane on the analysis slide defined by the test pattern or by the image of the surface of the slide or of the lamella.

The image acquisition apparatus 16 allows the sample 4 to be <<scanned>> with a very fine resolution and images in white light may be obtained from plate 8. The analysis plate 8 is scanned line by line as proposed by many industrialists. Thus, each acquired image represents a strip 18 with a predefined width of the analysis plate 8, for example a width of small value is selected in order to obtain a large number of images and therefore a better resolution. The images placed side by side give the possibility of obtaining an image of the entirety of the sample plate, or <<large field>> images, and therefore of the entirety of the sample in order to form a virtual analysis plate 2 as illustrated in step E of FIG. 1. If necessary, with the acquisition, it is possible to obtain images of the entirety of the sample plate at different thicknesses of the sample.

Thus, the images, obtained with a single and same apparatus and in a very simple way, are a true representation of the sample 4 associating a large amount of information in white light.

The digital data obtained with the apparatus 16 in white light are subject to computer processing in order to obtain a modified virtual analysis plate 2 formed with the image(s) having undergone polychrome virtual recoloration of the Papanicolaou, Schorr, May Grunwald Giemsa or Giemsa or monochrome type aiming at coloring the cells as described conventionally and known for cytological or morphological analysis by one skilled in the art.

According to a computer processing mode, the virtual recoloration is a Papanicolaou coloration, obtained as known for a long time and the semiology of which, widely described in the literature, allows possible recognition of cytoplasm and nuclear abnormalities for example corresponding to the presence of precancer or cancer cells. With this recoloration it is also possible to recognize the different types of cells and their number in order to determine the representative quality of the sample and for example to define whether the sample is representative or not. This virtual recoloration allows analysis of the virtual plate by a cell analysis method described below. As the Papanicolaou recoloration is virtual, coloration of the Feulgen type may be contemplated without any problem of compatibility.

The cell analysis is accomplished by an examination of the images of the sample by the physician or specialized technician entrusted with detecting pathological cells, in order to propose a diagnosis which will possibly trigger more extensive examinations or even a treatment. For quality assurance reasons, the presence of a physician or specialized technician is mandatory so that the detection of possibly pathological cells cannot be entirely automated.

Figure 3:
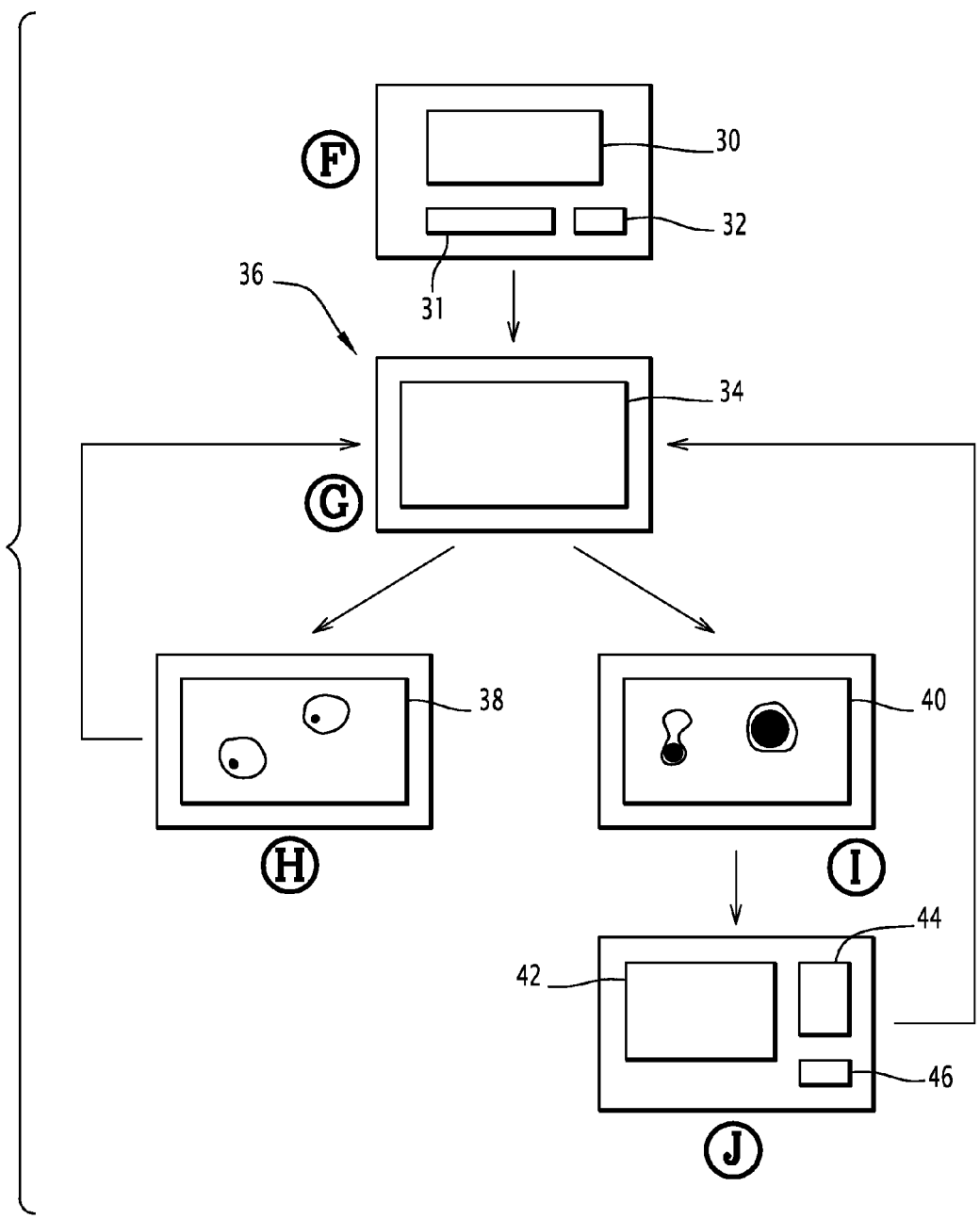
FIG. 3 is a diagram illustrating the different steps of analyzing a virtual plate.

With reference to FIG. 3, the process for viewing the images having undergone recoloration and for a diagnosis is detailed.

During a step F, the images 30 of the modified virtual analysis plate 2 formed with the image, or with images at different thicknesses of the specimen, having undergone virtual recoloration are projected on a display means such as a screen. The virtual restoration of the colors and of their intensity both for a cytoplasm and for the nucleus may be adjusted so as to correspond as closely as possible to the habits of each reader, i.e. the physician or specialized technician in terms of intensity and quality of coloration.

Information 31 on the patient may be associated with the virtual analysis plate 2 by entering this information into a database and associating them with the image, or with the images at different thicknesses, of the sample 4 corresponding to the patient on which this sample 4 was taken, after authorization from the operator, for example by actuating a virtual button 32 during step F.

The sample images 34 are scrolled under the eyes of the physician or specialized technician for examination during a step G. Scrolling of the images 34 is organized by the computer system and is accomplished automatically. Each image 34 is displayed full field without display of additional data in order to avoid dispersing the attention of the physician or specialized technician during the analysis (or <<screening>>), and this for a predetermined time calculated in order to allow the physician or specialized technician to observe the entirety of each projected image and to detect a possible abnormality in an image. The display time of each image may be adjusted by the physician or specialized technician depending on his/her skills or depending on other information. For example, if the sample was taken for a patient <<at risk>> having a greater probability of exhibiting pathological cells, the display time may be adjusted so as to be longer in order to carry out a more thorough examination of the sample.

The images 34 which are scrolled are therefore those of the modified virtual analysis plate, formed with the image or with images at different thicknesses, having been subject to virtual recoloration of the Papanicolaou, Schorr, May Grunwald Giemsa or Giemsa type. The images 34 under this coloration give the possibility of detecting the possible presence of abnormalities for example corresponding to the presence of precancer or cancer cells and the semiology of which known for a long time is widely described in the literature, and of checking whether the sample actually meets the Bethesda criteria, within the scope of cervical smearing for example. The software may also acquire other information on the cell spreading. This information is linked to the image (or to the images at different thicknesses) by the computer system in order to complete the virtual analysis plate 2.

The physician or specialized technician observes each displayed image on the screen, and determines whether an abnormality is present or not. This detection may also be carried out automatically by the computer system by means of the image analysis software package.

In the case when neither the physician or specialized technician, nor the cell analysis computer system detects any abnormality in the displayed image 38 during a step H, the diagnostic method continues by projecting the next image after a display time adjusted beforehand has elapsed.

According to an embodiment of the cell analysis, a step is provided during which the computer system automatically stops the scrolling of the images on an image on which no abnormality is detected and waits for validation by the physician or specialized technician in order to restart the scrolling. By stopping on such an image, it is possible to analyze in detail so-called reference images in order to confirm what is considered as a normal sample. This stopping on so-called normal images may be accomplished randomly or after a certain number of displayed images. The description of the detailed analysis of an image is made below in connection with the analysis of an image having an abnormality.

If an abnormality is detected in the image 40 by the physician or specialized technician and/or the computer system, the method continues by interrupting the scrolling of the images 36 during a step I.

Interruption of the scrolling is accomplished automatically by the computer system if the latter detects an abnormality or manually by the physician or specialized technician if he/she desires to observe an image in more detail or if he/she locates an abnormality.

The image 42 is then displayed with an greater enlargement level in order to view the abnormality in detail. For example, the display of the images may be accomplished with an enlargement level of ×10 during the scrolling and may be doubled (×20) in the case when an abnormality is detected, as illustrated by step J of FIG. 3.

The display of the image containing an abnormality may be accompanied by the display of information 44 on the displayed sampling area and/or on the entirety of the sample and/or on the patient on which the sample was taken and/or on the result of additional examinations made on the sample, notably molecular biology examinations.

The displayed image under virtual recoloration, and for which the scrolling has been interrupted, is associated with the image of the same area without virtual recoloration. With this display, it is possible for the physician or specialized technician to refine his/her analysis of the displayed cells and to either confirm or not if some of them are possibly pathological. Further, with the display of the image without virtual recoloration, other information may be displayed simultaneously such as quantitative data, spectra or information on the patient on which the sample was taken, etc, With this finer analysis coupled with the automated stopping of the scrolling it is possible to reduce the number of false negatives. Further within the scope of cervical smearing for example, by having the diagnosis checked by the physician or specialized technician, of the areas selected by the system, it is possible to retain a high level of specificity of the cytological diagnosis in this case. Consequently, the sensitivity and specificity criteria of screening smearing become closer and higher.

The restarting of the scrolling can only be controlled by the physician or specialized technician for example by pressing on a validation button 46. This provides the guarantee that if the scrolling was interrupted automatically, the displayed image and possibly having an abnormality has been examined by a physician or specialized technician. The same applies for the displayed normal images.

During the course steps F to J, the physician or specialized technician may freely perform magnification of particular areas of the displayed image, both on the image with virtual recoloration and on the image without virtual recoloration. The physician or specialized technician may also switch from the image with virtual recoloration to the image without virtual recoloration as desired.

The method described above allows fast and efficient analysis of samples, reducing the risk of <<false negatives>>.

Further, the experience of physicians or specialized technicians in terms of diagnosis quality and especially specificity is preserved because of the recognition of the colors and of their intensity related to the virtual images of treated and displayed cytological and/or histological preparations.

With the method it is also possible to adapt the analysis plate to the preferences of the physician or specialized technician in charge of the analysis. Indeed, the physician or specialized technician may select the intensity and the coloration of the virtual analysis plate as he/she pleases.

With the method, it is further possible to acquire images of better resolution in grey levels than by a color acquisition.

Further, the method allows acquisition at different thicknesses in the specimen, while retaining clear, accurate images by means of the reference plane with which it is possible to get rid of the problem of horizontal adjustment of the apparatus. Thus, even if the apparatus does not allow sufficient horizontal scrolling of the slide by lack of adjustments, it is possible to obtain a quality image which may interpreted. The adjustment of the apparatus no longer requiring such great precision, the method provides a first saving in time for the digitization.

The acquisition in grey levels also allows faster acquisition than in color, notably during the acquisition at different thicknesses in the sample. Indeed, when the physician or specialized technician in charge of the analysis desires to produce for example shots every 2 µm in the thickness of a cell i.e. 10 µm, the acquisition is five times longer, which is too long for a single specimen. In grey levels, the acquisition time is substantially reduced.

Finally, this method allowing recoloration of a virtual analysis plate allows savings in staining agent while guaranteeing fast and efficient analysis of the samples.

The invention claimed is:

1. A method for preparing a virtual analysis plate for a cytological sample positioned on an analysis plate, comprising the following steps:
    treating the sample in order to allow pathological cells to be differentiated from healthy cells of the sample,
    positioning the sample on a slide, and a lamella on the slide, wherein the sample is positioned between the slide and the lamella;
    locating a reference plane for image acquisition, said reference plain being selected from the upper surface of the slide or by the upper surface of the lamella;
    carrying out a first acquisition of images of the sample positioned on the analysis plate so as to obtain a first plurality of images, each image representing an area of the analysis plate, said images being placed side by side so as to form an image of the entirety of the sample in order to create said virtual analysis plate; and
    carrying out a second acquisition of images of the sample, said second acquisition being carried out at a thickness defined with respect to the reference plane that is different from that of the first acquisition, so as to obtain a second plurality of images, the second plurality of images corresponding to a section of the sample made at a different depth than the first plurality of images.

2. The method according to claim 1, wherein the location of the reference plane of the analysis plate is achieved by acquiring a topographic image of the slide or of the lamella.

3. The method according to claim 1, wherein the analysis plate comprises at least one test pattern laid out so as to locate the reference plane for the image acquisition regardless of the thickness of the sample positioned on the analysis plate.

4. The method according to claim 3, wherein the analysis plate comprises at least four test patterns positioned around the sample.

5. The method according to claim 3, wherein said at least one test pattern is printed on the analysis plate.

6. The method according to claim 1, wherein the thickness of the sample is adjustable.

7. The method according to claim 1, further comprising a step of superposing data of the acquired first and second images and data of the acquired images that has been modified by processing said acquired images, so as to produce a single large field virtual image.

8. The method according to claim 1, wherein the acquisition of first and second images of the sample positioned on the analysis plate is carried out according to a grey level scale.

9. The method according to claim 1, further comprising the following step:
    processing the acquired first and second images so as to obtain a virtual restitution of the colors and the intensity of the colors of the cytoplasm and/or the nucleus of the cells of the sample, wherein said colors and said intensity can be modified according to preferences of a person preparing the virtual analysis plate.

10. The method according to claim 1, wherein treating the sample comprises nuclear staining or cytological staining, so as to make the cytoplasm almost transparent and enhance the contrast between the nucleus and/or cytoplasm RNA of the cells and the cytoplasm.

11. The method according to claim 9, wherein the processing of the first and second acquired images corresponds to polychrome recoloration of Papanicolaou, Schorr, May Grunwald Giemsa, or Giemsa, or a monochrome type of said acquired images.

12. The method according to claim 9, wherein the level of virtual restitution of the acquired first and second images is adjustable.

13. The method according to claim 1, further comprising displaying the virtual analysis plate.

14. The method according to claim 13, further comprising:
    automatically scrolling the acquired images of the sample displayed as the virtual analysis plate, and
    automatically stopping the scrolling if at least one abnormality, which may signify the presence of a pathological cell, is detected by an automatic analysis system.

15. The method according to claim 14, further comprising, after stopping the scrolling, enlarging the at least one abnormality and secondarily displaying information pertaining to one or more of: the displayed sampling area, the entirety of the sample, the patient on which the sample was taken, and a result of additional examinations made on the sample.

16. The method according to claim 13, further comprising enlarging the displayed virtual analysis plate in order to allow viewing of a detail of said plate.

17. The method according to claim 4, wherein said at least four test patterns are printed on the analysis plate.

18. The method according to claim 10, wherein the processing of the first and second acquired images corresponds to polychrome recoloration of Papanicolaou, Schorr, May Grunwald Giemsa, or Giemsa, or a monochrome type of said acquired images.

* * * * *